United States Patent [19]

Saito

[11] 4,200,799

[45] Apr. 29, 1980

[54] TOMOGRAPHING DEVICE

[75] Inventor: Kiyoto Saito, Yokohama, Japan

[73] Assignee: Tokyo Shibaura Electric Co., Ltd., Kawasaki, Japan

[21] Appl. No.: 815,360

[22] Filed: Jul. 13, 1977

[30] Foreign Application Priority Data

Jul. 15, 1976 [JP] Japan .................................. 51/84107
Oct. 8, 1976 [JP] Japan ................................ 51/121012
Dec. 28, 1976 [JP] Japan ................................ 51/160211

[51] Int. Cl.² ...................................................... G03B 41/16
[52] U.S. Cl. .................................. 250/445 T; 250/511
[58] Field of Search ................... 250/445 T, 361, 363, 250/511, 512, 513

[56] References Cited

U.S. PATENT DOCUMENTS

| | | | |
|---|---|---|---|
| 3,954,098 | 5/1976 | Dick et al. ........................ | 250/445 T |
| 3,973,127 | 8/1976 | Matsuda et al. .................. | 250/445 T |
| 4,048,503 | 9/1977 | Taylor .............................. | 250/445 T |
| 4,048,505 | 9/1977 | Hounsfield ....................... | 250/445 T |
| 4,049,967 | 9/1977 | Berger et al. ..................... | 250/445 T |
| 4,115,696 | 9/1978 | Truscott ........................... | 250/445 T |
| 4,134,020 | 1/1979 | Zonneveld ....................... | 250/445 T |

FOREIGN PATENT DOCUMENTS

1478123 6/1977 United Kingdom .

*Primary Examiner*—Bruce C. Anderson
*Attorney, Agent, or Firm*—Finnegan, Henderson, Farabow, Garrett & Dunner

[57] ABSTRACT

A computed tomograph system comprises a radiation source for emitting a fan-shaped beam of penetrating radiation of included angle α, and a radiation detector comprising a plurality of radiation detection cells on which the fan-shaped beam falls. Between the radiation source and the radiation detector a subject to be examined is placed. The radiation source and radiation detector are mounted on a support frame. The support frame is movable along an axis defined between the radiation source and the subject and rotatable with the subject as a center. The support frame is moved by a shifting mechanism so as to be adjustable in accordance with the size of the area of the subject to be examined or the size of the region of interest, and rotated by a rotating mechanism. The radiation source has a variable diaphragm for permitting the included angle α of the fan-shaped beam to be varied according to the size of the area of the subject and a variable slit for varying the thickness of the fan-shaped beam. The radiation detector has a variable collimator on a radiation incident plane to permit the collimating width of the fan-shaped beam path to be varied according to the width of the slit opening.

17 Claims, 14 Drawing Figures

TOMOGRAPHING DEVICE

This invention relates to an improvement in a tomographing device. A tomographing device, for example, computed tomograph scanner (hereinafter referred to as a CT Scanner), is disclosed in U.S. Pat. Nos. 3,983,398, 3,965,357 etc, as a tomographing device for photographing the cross-section of a subject such as a human being etc. Briefly stated, the tomographing device is a device for emitting radiation in a plurality of directions toward the outer surface of the area of a subject from which a tomographic image is to be obtained, detecting the dosage of radiation passed through the subject by means of highly sensitive radiation detection cells to obtain data representing radiation absorptivity, or permeability, and processing the detection data by a computer to display a corresponding tomographic image on a CRT.

The scanning system described herein is of the general type disclosed in U.S. Pat. No. 3,965,357 in which a transverse-index scanning system using a penetrating radiation beam is adopted. A recent trend is toward an index scanning system using a fan-shaped beam of penetrating radiation as shown in U.S. Pat. No. 3,983,393. Since the tomograph used in the index scanning system includes a radiation detector comprised of a plurality of radiation detection cells, it is possible to obtain a plurality of data signals representing radiation absorptivity or permeability by subjecting the area of the subject to radiation in the form of a fan-shaped beam. In consequence, it is possible to obtain those multi-direction data for a brief period of time which are required to obtain a tomographic image of the subject.

However, there is a problem that, where the to-be-examined area of the subject or the region of interest to be examined is varied, a data for permitting reproduction of an excellent image is varied in number. A radiation source, subject and radiation detector in the tomographing device of the index scanning system are arranged such that a substantially fan-shaped beam of penetrating radiation from the radiation source is passed through the to-be-examined area of the subject and falls onto the radiation detector. If a small area to be examined, for example, the head of a human being is tomographed, since not all, but some of the fan-shaped beam is passed through the head of the human being, data obtained from one exposure to the fan-shaped radiation beam is decreased, failing to reproduce an excellent tomographic image on the CRT.

If, therefore, it is desired to obtain an excellent tomographic image of the head, it is necessary to substantially increase the effective data by increasing the number of times the radiation beam is emitted. In this case, however, the head is subjected to a corresponding amount of radiation exposure. This situation must be avoided. Furthermore, an increase in the dosage of radiation exposure requires a corresponding length of time to reproduce a tomographic image. During such a time, there is a few that the subject will be moved, even if slightly. Even a slight movement will contribute significantly to loss of resolution of image.

One object of this invention is to provide a tomographing device which is capable of reproducing an excellent image irrespective of the size of the area of a subject or the size of the region of interest.

Another object of this invention is to provide a tomographing device which provides an effective quantity of tomographic data during a brief period of time.

Another object of this invention is to provide a tomographing device which can restrict the amount of radiation exposure to a minimum level.

According to this invention there is provided a CT scanner, comprising a radiation source for exposing a subject to a substantially fan-shaped pattern of beams of penetrating radiation; a radiation detector disposed opposite to the radiation source with the subject therebetween to detect the radiation penetrating the subject and to convert the detected radiation intensity into electrical signals; signal processing means for determining the pattern of radiation absorption coefficients included in the exposed cross-sectional area of the subject based on the electrical signals produced by the radiation detector; means for rotating the radiation source and the radiation detector around the subject to scan the cross-sectional area; and means for shifting the rotation loci of the radiation source and the radiation detector relative to the subject to position the cross-sectional area within the fan-shaped radiation pattern so as to intersect a maximum number of beams.

This invention will be further described by way of example by referring to the accompanying drawings in which.

Figure 1:
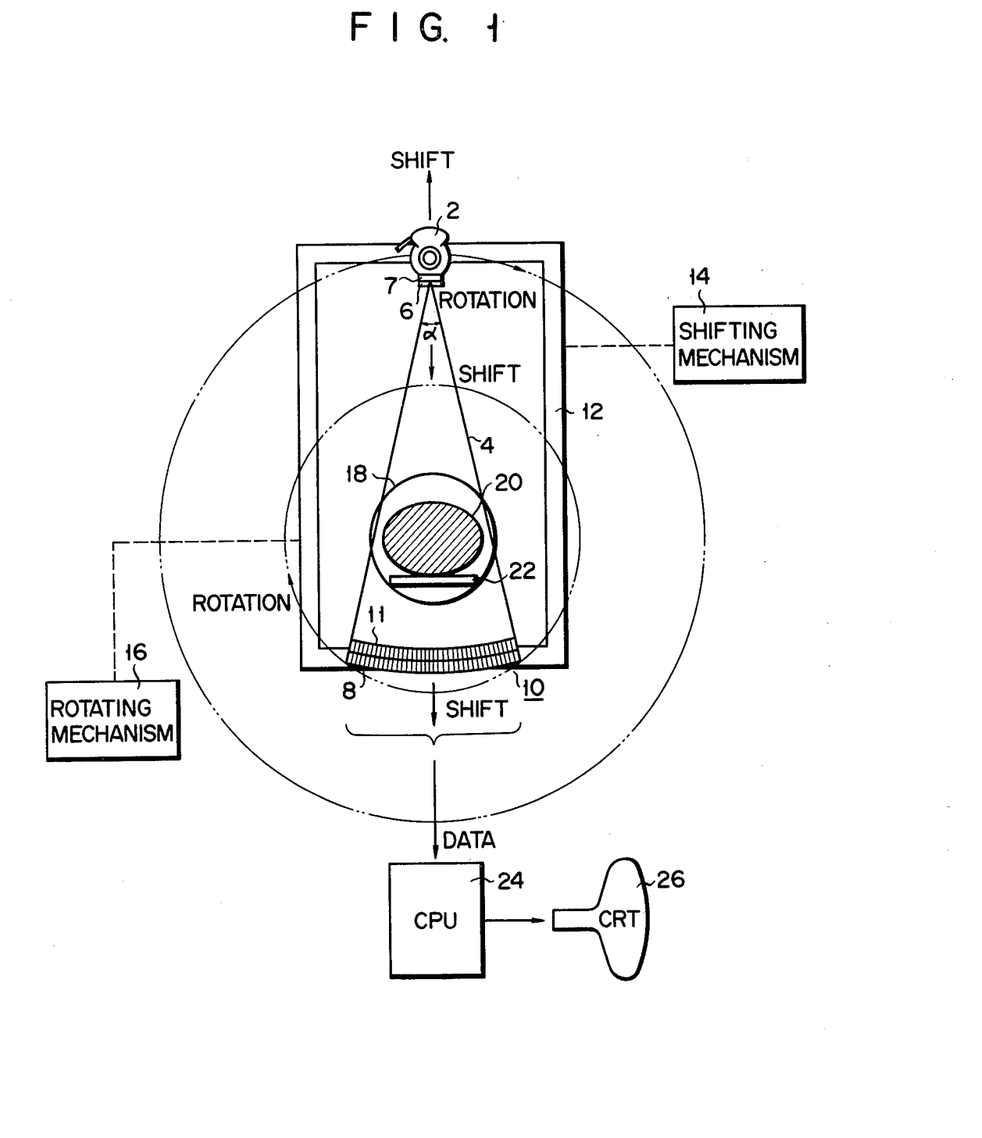
FIG. 1 is a schematic view showing one embodiment of a tomographing device.

A tomographing device which uses a fan-shaped beam of penetrating radiation will be schematically explained by referring to FIG. 1.

In FIG. 1, a reference numeral 2 depicts a radiation source such as an X-ray source, γ-ray source etc. A diaphragm 6 and slit 7 are arranged in a radiation emitting outlet (not shown) to permit the fan-shaped beam of penetrating radiation 4 (hereinafter referred to as the fan-shaped beam) to be emitted at a predetermined included angle α. The diaphragm 6 herein defined is intended to mean a device for setting the included angle α at which the fan-shaped beam is restricted, and the slit 7, a device for restricting the thickness (perpendicular to the plane of the drawing) of the fan-shaped beam 4. A radiation detector 10 comprising a plurality of radiation detecting cells 8 are arranged opposite to the radiation source 2. A collimator 11 is arranged on that plane of the radiation detector 10 on which the fan-shaped divergent radiation is incident. The collimator 11 herein defined is intended to cause the fan-shaped radiation from the radiation source 2 to be divided into a plurality of radiation beam paths whereby the fan-shaped beam 4 can be said to comprise a plurality of individual diverging beams which are incident onto the corresponding radiation detecting cells 8 in the radiation detector 10. Where the radiation source 2 is an X-ray source, the radiation detector cell 8 is an X-ray detecting element comprising a combination of scintillator and photomultiplier. The radiation detector 10 may be, for example, a gas detector or semiconductor detector. The radiation source 2 and the radiation detector 10 are secured to a support member 12 in a manner to be spaced a predetermined distance apart from each other, and moved by a shifting mechanism 14 while spaced a predetermined distance apart from each other. Since the support member 12 is rotated by a rotating mechanism 16 the radiation source 2 and radiation detector 10 are rotated in a manner to be held in a predetermined relative relation. The rotation center of the support member 12, i.e. the rotation center of the radiation source 2 and radiation detector 10 is not varied even when the support member 12 is moved by the shifting mechanism 14. The support member 12 is supported on a support (not shown in FIG. 1) so that the rotation loci of the radiation source 2 and radiation detector 10 on the support member 12 are varied by the movement of the support member 12. A cavity or opening 18 is provided at the rotation center area of the support member and a couch 22 is disposed in the cavity 18 to permit a to-be-examined subject 20 of various sizes to be placed thereon.

With the tomographing device according to this invention, the diaphragm 6 may be a fixed diaphragm adapted to maintain the included angle α of the fan-shaped beam 4 constant; the slit 7, a fixed slit adapted to maintain the thickness of the fan-shaped beam constant; and the collimator 11, a fixed collimator adapted to maintain constant the width of the fan-shaped beam paths incident onto the radiation detector 8. In a preferred embodiment the diaphragm 6 is a variable diaphragm for permitting the included angle α of the fan-shaped beam 4 to be varied as will be later described, the slit 7 is a variable slit for permitting the thickness of the fan-shaped beam 4 to be varied, and the collimator 11 is a variable slit for permitting the width of the fan-shaped beam 4 to be varied in coaction with the variable slit 7.

The collimator 11 may be disposed between the radiation source 2 and the couch 22 in addition to being disposed between the radiation detector 10 and the couch 22, as shown in FIG. 1.

The tomographing device according to this invention has the above-mentioned schematic arrangement. The tomographing device further includes a calculation control unit 24 (hereinafter referred to as the CPU) for analyzing data sent from the radiation detector, and a CRT display 26 (hereinafter referred to as the CRT) for displaying a tomographic image of the subject based on the analyzed data.

Figure 2A:
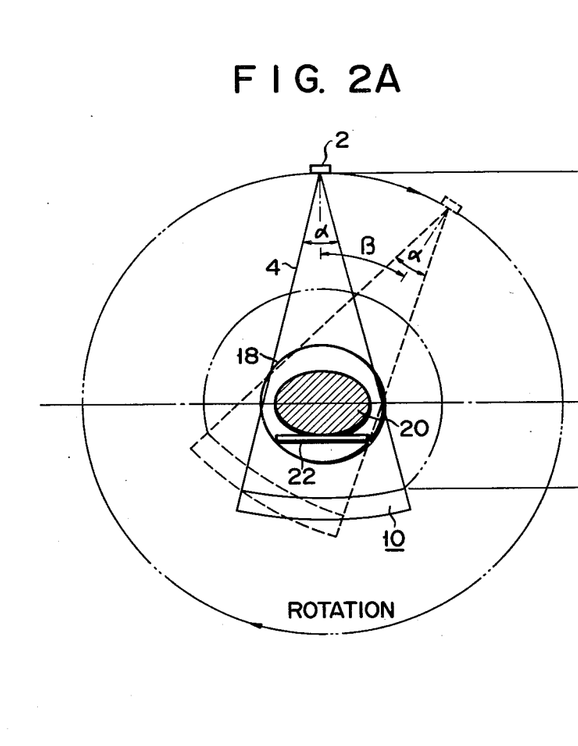
FIGS. 2A to 2B, 3 and 4A to 4B are views for explaining the operation of a tomographing device which is according to this invention.

The tomographing device is operated as follows:

When the to-be-examined subject 20 having a region of interest of a predetermined size, for example, a human body is placed on the couch 22, the support member 12 is moved by the shifting mechanism 14 and stopped at a predetermined position to permit the fan-shaped beam 4 from the radiation source 2 to penetrate a predetermined area of the human body 20 so that a corresponding tomographic image can be obtained. Then, the supporting member 12 is rotated by the rotating mechanism 14 and thus the radiation source 2 and radiation detector 10 are rotated as shown in FIG. 2A, describing predetermined low circumferentially disposed about the human body 20. While the support member 12 is being rotated, the fan-shaped beam 4 is intermittently emitted from the radiation source 2 toward the human body 20 at a predetermined interval, for example, at a rate of once for each rotation angle γ°. Most of the fan-shaped beam 4 so emitted is passed through the human body 20 and falls onto a plurality, for example DN number, of radiation detection cells 8. By permitting the fan-shaped beam 4 having a predetermined included angle α to be emitted once for each rotation angle γ°, the radiation detector 10 detects DN number of radiation intensity output signals. Since the fan-shaped beam 4 is emitted at a rate of β/γ times for β° rotation of the support member 12, the radiation detector 10 detects N=DN×β/γ number of radiation intensity output signals.

The scanned N number radiation intensity output signals obtained from the radiation detector 10 are delivered to CPU 24 where they are analyzed or processed in terms of radiation absorptivity corresponding to that area of the human body 20 from which a tomographic image is obtained. CPU 24 converts such radiation absorptivity data to a video signal for supply to CRT 26. CRT 26 displays a tomographic image based on the video signal corresponding to the area of the human body. It should be noted that analyzing radiation absorptivity may be carried out by using special type of memory tube as is shown in the U.S. Pat. No. 4,021,673.

Figure 2B:
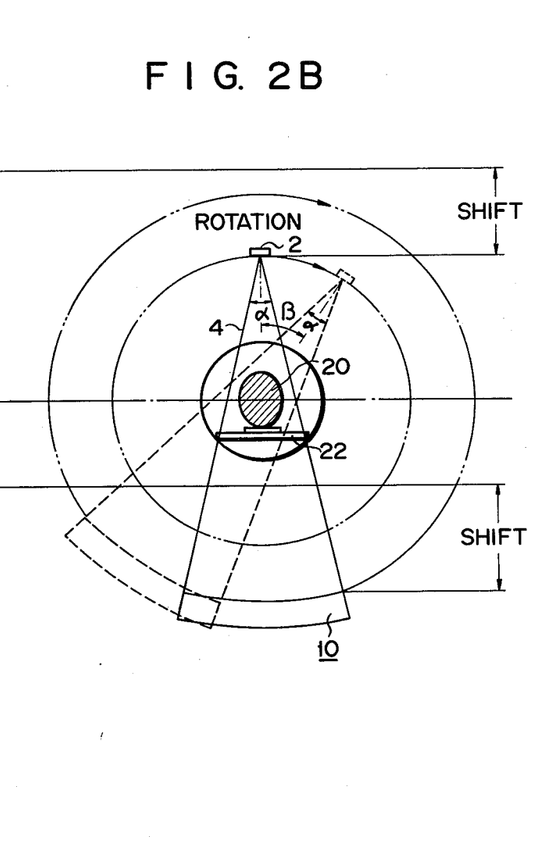

However, all of N number of radiation intensity output signals detected at the radiation detector 10 are not processed, by the CPU, as effective data for reproducing such a tomographic image, and only those radiation intensity signals passed through the human body 20 are processed as effective beams. Those data incident directly onto the radiation detection cells 8 without being passed through the human body 20 are processed by CPU 24 as ineffective data. A part of this data is, however, effectively used for compensation of detector sensitivity. This is because those radiation beams which are directly incident onto the radiation detection cells 8 do not include any data on the absorption characteristics of the human body, since they are not passed through the human body 20.

Where as shown in FIG. 2A most of the fan-shaped beam 4 passes through the trunk of the human body 20, a number of effective output signals are obtained at the radiation detector 10. Where, however, the to-be-examined area of the subject or the region of interest becomes small, for example, when the region is shifted from its trunk to its head or its liver, the effective data obtained at the detector 20 are prominently decreased, resulting in an increase in ineffective data. As a result, the tomographic image displayed by CRT 26 is lowered in its quality or resolution.

Where in the tomographing device of this invention the area of the to-be-examined subject 20 or the region of interest becomes small, the shifting mechanism 14 is operated to cause the support member 12 to be moved as shown in FIG. 2B so that the relative position of the radiation source 2 and radiation detector 10 is varied with respect to the subject without varying the distance between the radiation source 2 and the radiation detector 10. In consequence, most of the fan-shaped beam 4 emitted from the radiation source 2 as shown in FIG. 2B passed through the to-be-examined subject 20 or the region of interest to permit the radiation detector 10 to adequately detect data which are effective to reassemble the tomographic image. Only a small predetermined portion of the radiation is allowed to bypass the subject for use in generating sensitivity compensation data signals. In other words, the amount of radiation, i.e., the number of individual beams, passing through the subject is maximized whereupon an image of maximum quality or resolution can be produced.

Figure 3:
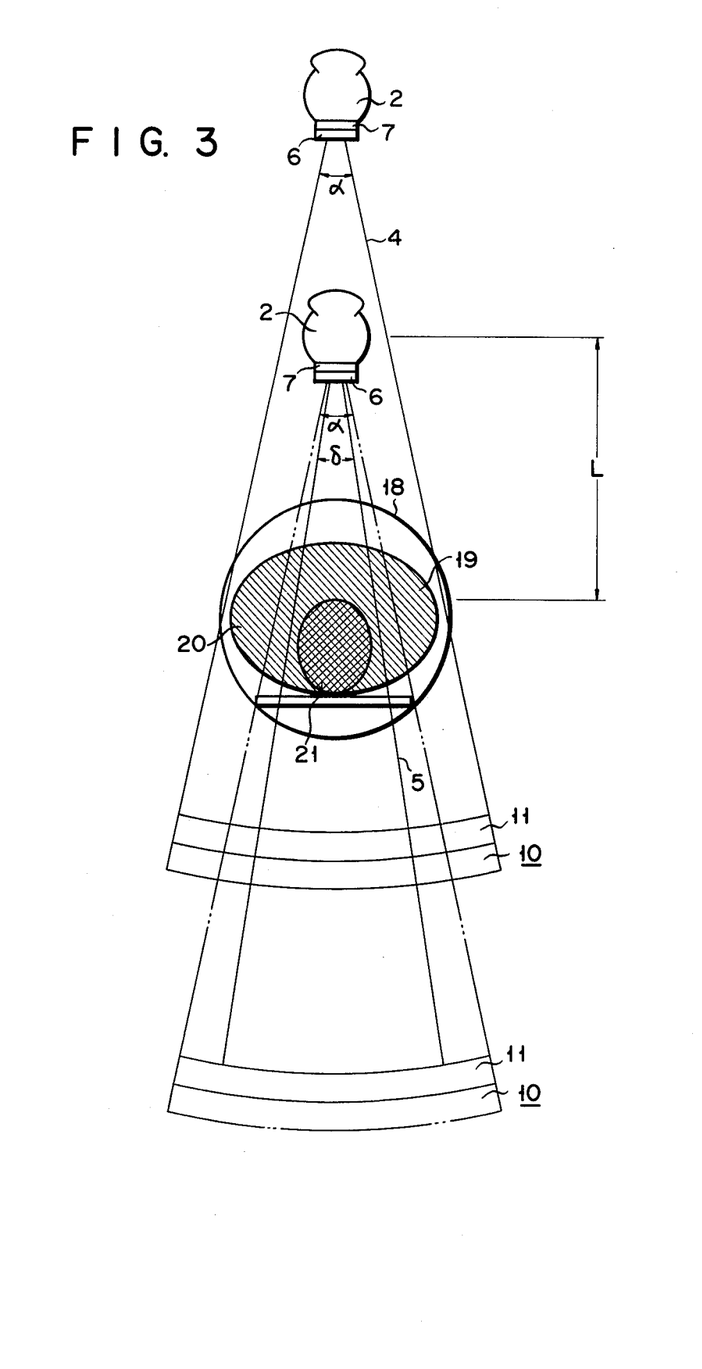

In the preferred embodiment of this invention the diaphragm 6 is of a variable type. The tomographing device equipped with the shifting mechanism 14 enables the distance between the to-be-examined subject 20 and radiation source 2 to be adjusted. However, such a distance should fall within the limit of the U.S. HEW Standard (defining an allowable exposure dosage). That is, where the subject 20, for example, a head is to be examined with the radiation source 2 as an X-ray source, it is necessary that the head does not suffer a bad effect from an X-ray emitted from the X-ray source, due to the X-ray source 2 being very near to the head. Since, however, the distance between the radiation source 2 and the to-be-examined subject 20 is restricted within a predetermined range, it is impossible to adequately remove ineffective data from those data derived from the radiation detector i.e. sufficiently increase the proportion of effective data to ineffective data. This is the reason why in this preferred embodiment a variable diaphragm is provided. Where the area of the to-be-examined subject is a relatively large area, for example, the trunk in FIG. 3, the variable diaphragm 6 stops down the fan-shaped beam 4 emitted from the source 2 so as to obtain an included angle $\alpha$. Where, on the other hand, the area of the to-be-examined subject is a small area, for example, the head 21, the radiation source 2 is moved by the shifting mechanism 14 close to the head 21 with a predetermined distance L left between the source 2 and the head 21. At the same time the opening of the diaphragm 6 is narrowed. As a result, the fan-shaped beam 5 emitted from the radiation source 2 is stopped down by the variable diaphragm 6 so as to obtain an included angle $\delta$ smaller than the included angle $\alpha$. The fan-shaped beam 5 of included angle $\delta$ is incident onto the radiation detector 10 so that the proportion of ineffective data to effective data as obtained from the radiation detector 10 can be decreased to a very small extent. By preliminarily providing CPU 24 with data on the size of the opening of the variable diaphragm 6, CPU 24 can distinguish between effective and ineffective data sent from the radiation detector 10, making it easy to improve the resolution capability of the tomogram.

Figure 4A:
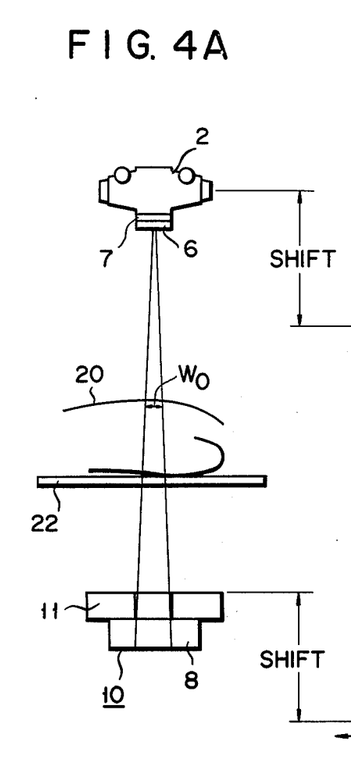
Figure 4B:
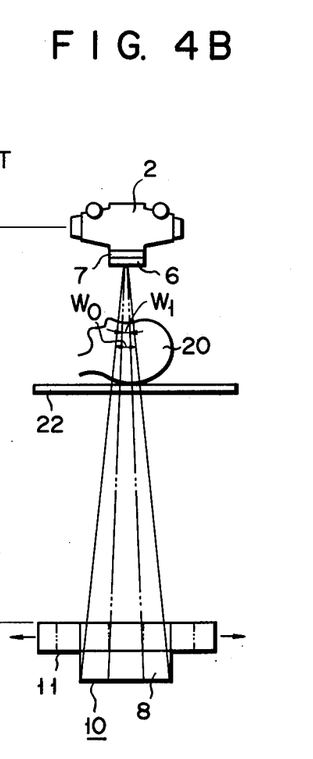

In the preferred embodiment of this invention the slit 7 is of a variable dimension and the collimator 11 is also a variable dimension dimension. When the area under examination is varied as shown in FIGS. 4A and 4B and in consequence the distance between the radiation source 2 and the to-be-examined subject 20 is varied, the thickness of the fan-shaped beam 4 passed through the to-be-examined subject 20 i.e. the slice thickness of the to-be-examined subject from which a tomographic image is obtained is varied from $W_0$ to $W_1$. Where the radiation source 2 is moved close to the to-be-examined subject 20 with a predetermined distance L (FIG. 3) left therebetween, the opening of the variable slit is widened, maintaining the slice thickness $W_0$ always constant. Since there is a clear correspondence between the obtained image and the anatomical position of the to-be-examined subject, diagnosis can be made based on the obtained image without taking the variation of the slice thickness into consideration. Since, however, even if the slice thickness is always maintained constant the radiation detector 10 spaced a predetermined distance apart from the radiation source 2 is also moved by the shifting mechanism 14, there is less chance that all the beam passed through the to-be-examined subject 20 or the region of interest will fall onto the radiation detector 10. As a result, the tomographic image data on the to-be-examined subject 20 becomes inaccurate. When, therefore, the variable slit 7 is widened as shown in FIG. 4B, the opening of the variable collimator 11 is thus also widened in a manner to correspond to the width of the opening of the variable slit 7. Since, even if the opening of the variable slit 7 is widened to permit the beam to be correspondingly widened the width of the variable collimator 11 is also widened, the beam all falls onto the radiation detector 10 through the variable collimator 11 and the data content of the detector output signals is not reduced.

The detailed forms of the above-mentioned variable diaphragm 6, variable slit 7 and variable collimator 11 will be explained by reference to FIGS. 7 to 12.

One embodiment of the tomographing device according to this invention will be explained below by referring to FIGS. 5 and 6.

Figure 5:
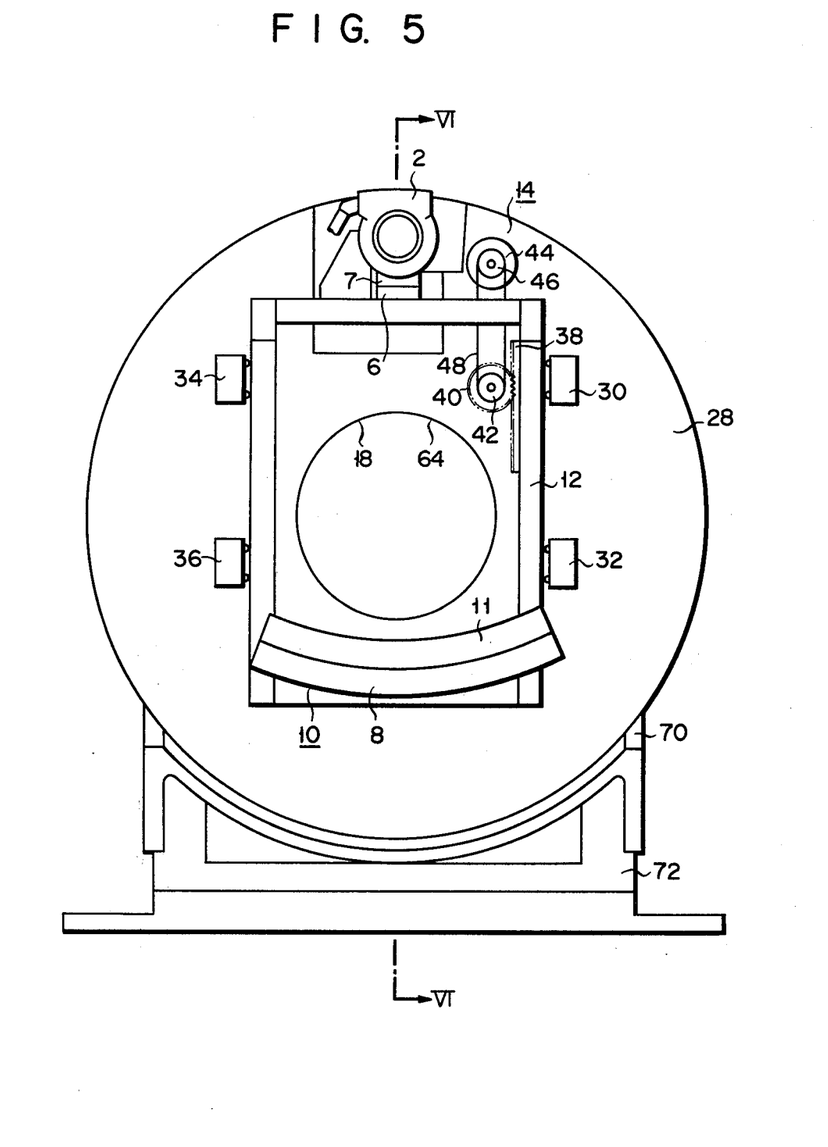
FIG. 5 is a schematic front view for showing the tomographing device which is according to one embodiment of this invention.
Figure 6:
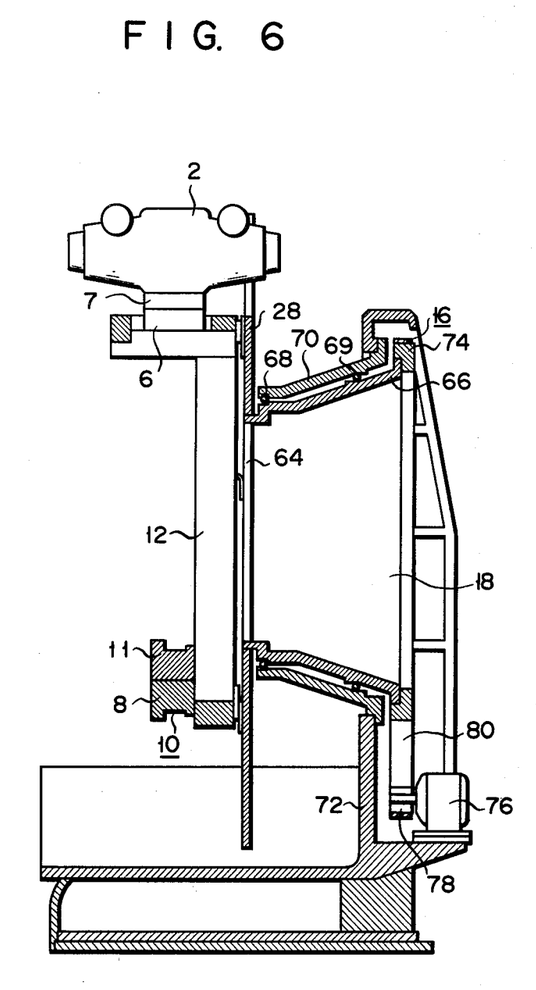
FIG. 6 is a cross-sectional view taken along line VI—VI in FIG. 5.

In FIGS. 5 and 6 is shown the tomographing device with the cover, couch 22 and the to-be-examined subject 20 all removed and the same reference numerals are employed to designate parts or elements corresponding to those shown in FIGS. 1 to 4. An X-ray tube 2 (radiation source), X-ray detector 10 and collimator 11 are mounted on a support member 12 such that the X-ray tube 2 is disposed opposite to the X-ray detector 10 and collimator 11. The support member 12 is shiftably mounted, through a sliding mechanism, on the front surface of a disc-like rotation support 28. The shifting mechanism comprises two pairs of guide rollers 30, 32 and 34, 36 secured to the rotation support 28 with one pair along one side of the support frame 12 and the other pair along the other side of the support frame; a rack 38 secured to the inner surface of said one side of the support frame 12; a gear 40 journaled on the rotation support 28 and meshing with the rack 38; a first sprocket 42 journaled integral with the gear 40; a motor 44 mounted on the support frame 12; a second sprocket 46 journaled on the motor 44; and a drive chain 48 adapted to be entrained between the first and second sprockets 44 and 46. Both the side surfaces of the support frame 12 are parallel to a line connecting the focal point of the radiation source 2 and the center of patient opening 64, and the guide rollers 30, 32 and 34, 36 are parallel to said side surfaces of the support frame 12. The opening 64 is provided at the central portion of the rotation support 28. A flared member 66 (FIG. 6) taking the form of a truncated cone is mounted on the rotation support 28 in a manner to be in alignment with the opening 64 and diverges rearwardly of the rotation support 28, thereby defining a cavity 18. The flared member 66 is rotatably supported through bearing 68, 69 on a fixed member 70 which in turn is mounted on a base 72. Since the flared member 66 is rotatably supported on the fixed member 70, the rotation support 28 mounted integral with the flared member 66 and the rotation frame 12 mounted in front of the support 28 are rotatably supported. A belt 80 is entrained between the outer marginal edge 74 of the flared member 66 and a pulley 78 of a motor 76 to permit a rotation force of the motor to be transmitted to the flared member 66.

The above-mentioned arrangement permits a smooth movement and rotation of the support frame 12 and also permits the rotation loci of the radiation detector 10 to be varied according to the size of the area of the to-be-examined subject without shifting the rotation center. When the motor 44 is rotated, its rotation force is transmitted to the gear 40 through the second sprocket 46, drive chain 48 and first sprocket 42 as shown in FIG. 5. The rotation force of the gear 40 is translated through the rack 38 on the support frame 12 into a linear motion. In consequence, the support frame 12 is moved along the guide rolls 30, 32 and 34, 36 i.e. along a line connecting the focal point of the radiation source 2 and the center of the opening 64. When the support frame 12 is moved to a predetermined position, the motor 76 is started to cause its rotation force to be transmitted to the flared member 66 through the pulley 78, permitting the rotation support 28 and support frame 12 shiftably mounted on the support 28 to be rotated at a predetermined speed. The rotation center remains unchanged even when the support frame 12 is shifted, and the rotation loci of the radiation source 2 and radiation detector 10 on the support frame 12 are varied.

The detailed forms of the variable diaphragm 6, variable slit 7 and variable collimator 11 will be explained by referring to FIGS. 7 to 12.

Figures 7, 8, 9:
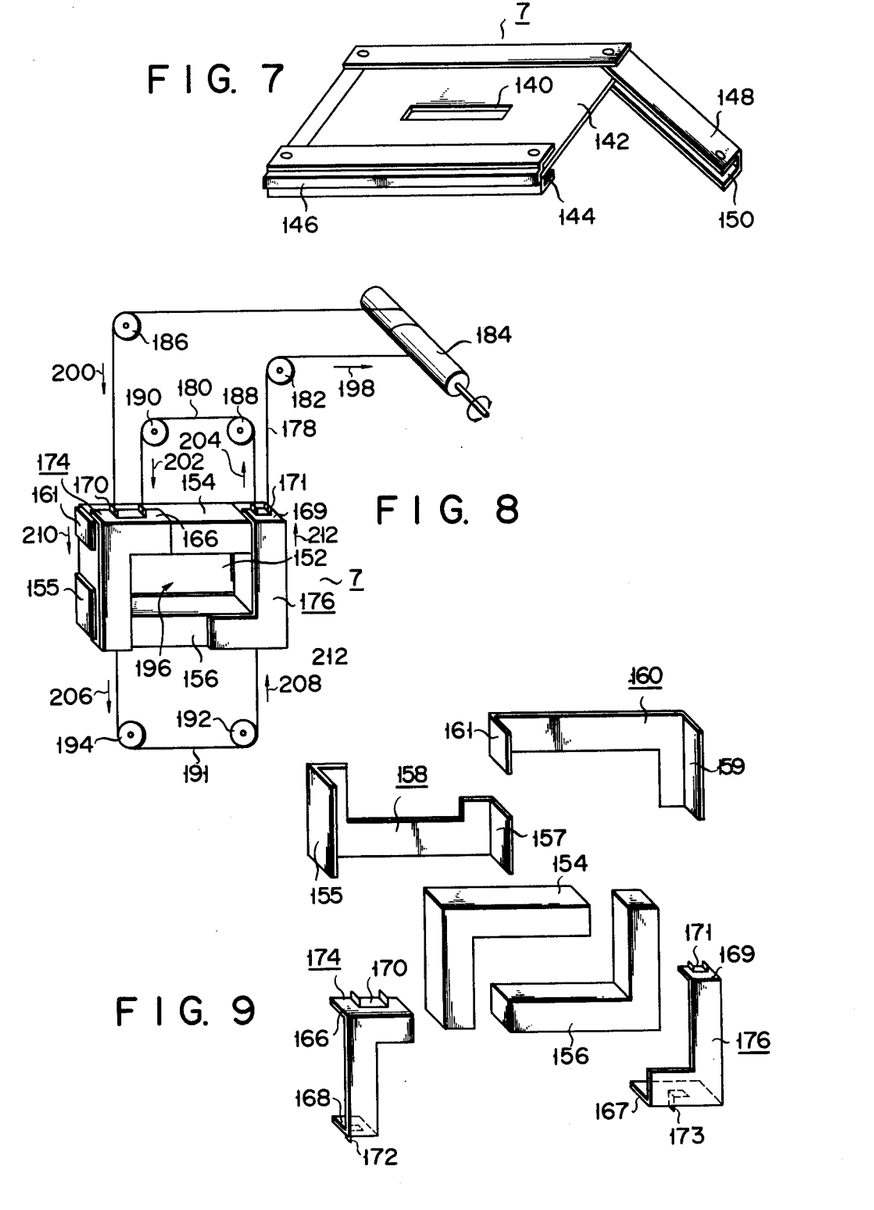
FIG. 7 is a perspective view showing one form of variable slit as incorporated in the scanner unit of the tomographing device.
FIG. 8 is a plan view schematically showing another form of variable slit as incorporated in the scanner unit of the tomographing device.
FIG. 9 is an exploded, perspective view showing the major section of the variable slit mechanism of FIG. 8.

A variable slit 7 shown in FIG. 7 includes a manually detachable slit plate 142 having a slit opening 140 of predetermined size, which may be replaced by another slit plate of a different size slit opening 140. The diaphragm 7 comprises the slit plate 142, a frame member 146 having an inwardly opening guide channel 144 through which the slit plate 142 is inserted as shown in FIG. 7, and a hinge 148 pivotally mounted on the frame 146 and constituting one side of the frame and having an inwardly opening channel 150. The slit plate 142 is positively assembled in the frame member 146 by inserting the slit plate 142 along the channel 144 of the frame member 146 into abutting engagement with the opposite channel portion of the frame member 146 and swinging the hinge 148 closed with respect to the frame to cause the channel 150 of the hinge 148 to be matingly engaged with the free end of the slit plate 142. In the variable slit 7 shown in FIG. 7 one slit plate 142 may be replaced by another slit plate of different slit opening so that a different thickness of beam 4 can be formed through such a slit.

A variable slit 7 shown in FIG. 8 permits the size of a slit opening 152 to be automatically varied by a motor (not shown). The major section of the slit 7 is shown in FIG. 9. In FIG. 9 the slit 7 comprises substantially L-shaped blocks 154 and 156, first and second frame members 158 and 160 of substantially the same configuration, and third and fourth frame members 174 and 176 of substantially the same configuration. The first frame member 158 has oppositely confronting bent portions 155 and 157 and the second frame member 160 has oppositely confronting bent portions 161 and 159. The third frame member 174 includes oppositely facing bent portions 166 and 168 having wire securing fittings 170 and 172, respectively, and the fourth frame member 176 includes oppositely facing bent portions 167 and 169 having wire securing fittings 173 and 171, respectively. The fittings 170 and 171 of the third and fourth frame members, respectively, are adapted to anchor two wires as shown in FIG. 8, and the fittings 172 and 173 of the third and fourth frame members 174 and 176, respectively, are adapted to anchor one wire as shown in FIG. 8. The first and second blocks 154 and 156 are so assembled that a rectangular opening (i.e. slit) is provided at the center of the block assembly. The blocks 154 and 156 are held in position such that the first and second blocks 154 and 156 are moved in one direction only. The blocks 154 and 156 are also held in position by the third and fourth frame members 174 and 176. The wire 178 anchored to the fitting 171 of the fourth frame member 176 is connected to the fitting 170 of the third flame member 174 through a first pulley 182, a take-up roll 184 connected to the motor, and a pulley 186. The other wire 180 anchored to the fitting 171 of the fourth frame member 176 is connected to the fitting 170 of the third frame member 174 through third and fourth pulleys 188 and 190. A wire 191 is connected, through fifth and sixth pulleys 192 and 194, between the fittings 173 and 172.

In the variable slit 7 shown in FIG. 8 the take-up roll 184 is rotated upon energization of the motor to cause the blocks 154 and 156 to be equidistantly moved, by means of the wire 178 on the take-up roll 184, toward and away from each other with a center 196 of the opening slit as a fixed center. For example, when the wire 178 on the first pulley 182 is pulled in a direction indicated by an arrow 198, the wire 178 on the pulley 186 is drawn in a direction indicated by an arrow 200. Simultaneously with the movement of the wire 178 the wire 180 is pulled in a direction indicated by arrows 202 and 204. The wire 191 also moves in a direction indicated by arrows 206 and 208 via the pulleys 192 and 194. In consequence, the first block 154 is moved relative to the block 156 in a direction indicated by an arrow 210, while at the same time the second block 156 is moved relative to the first block 158 in a direction indicated by an arrow 212. As a result, the size (i.e. the width) of the slit opening 152 is narrowed without shifting the center 196 of the slit opening 152. It is therefore possible to narrow the width of the fan-shaped beam 4 at the variable slit opening 152. When, on the other hand, the slit opening 152 is widened, the take-up roll 184 is rotated such that the wires 178, 180 and 191 are each pulled in a direction opposite that in which each of the wires 178 and 180 is moved.

Figure 10:
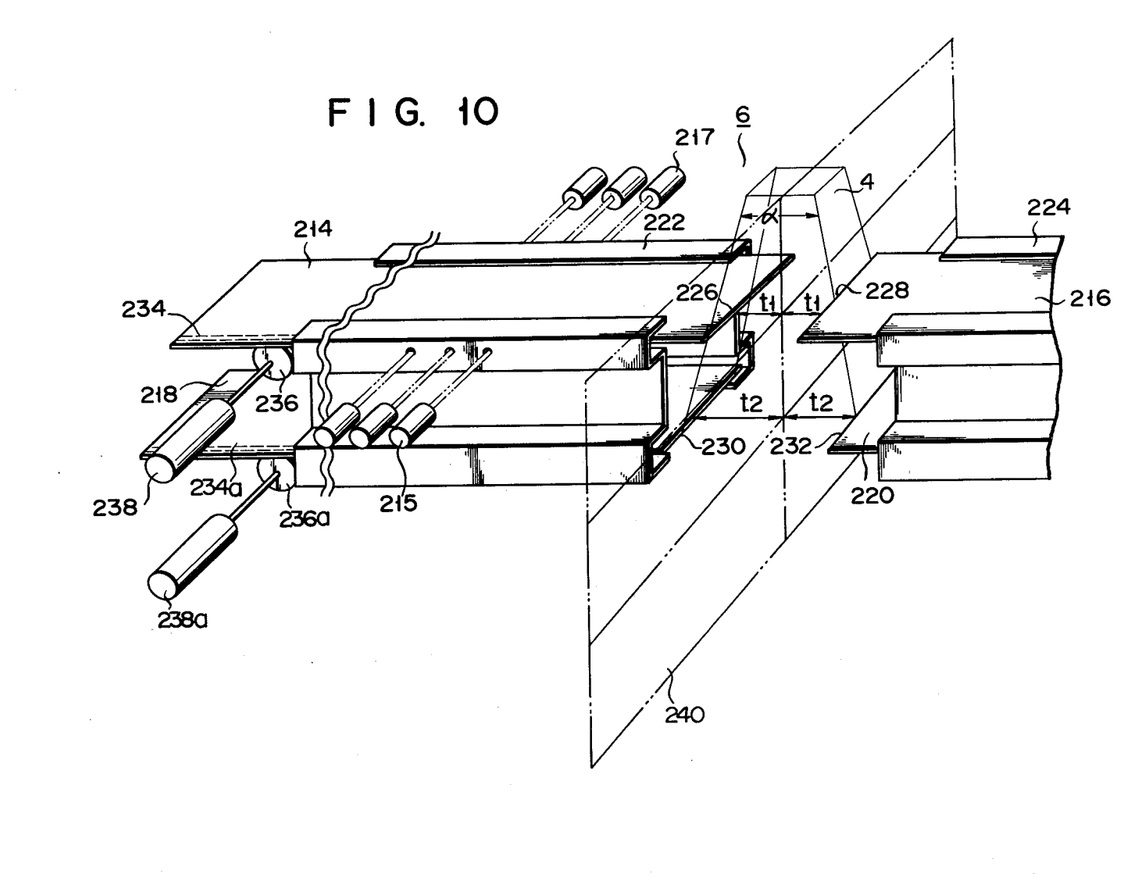
FIG. 10 is a perspective view schematically showing one form of variable diaphragm as incorporated in tomographing device.
Figure 11:
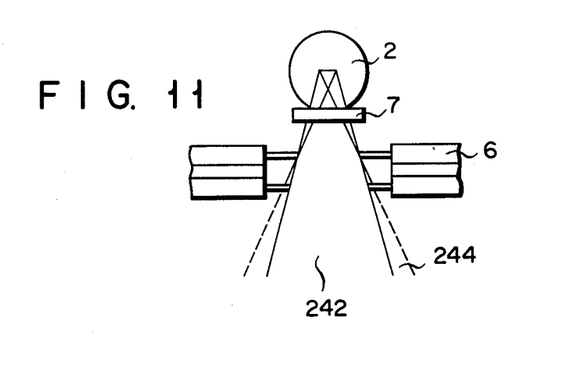
FIG. 11 is a view for explaining the operation of the variable diaphragm of FIG. 10.

A variable diaphragm 6 shown in FIG. 10 has four diaphragm plates 214, 216, 218 and 220. The included angle α of the fan-shaped beam 4 can be varied by relatively moving the diaphragm plates 214, 216, 218 and 220. In FIG. 10 first and second rectangular diaphragm plates 214 and 216 are located on the same plane, the first and second frames 222 and 224 are held to be fixed relative to each other. The first and second frames 222 and 224 are parallel to another plane on which the rectangular diaphragm plates 218 and 220 are moved relative to each other. The ends of the diaphragm plates 214 and 216, respectively, are moved equidistantly (for example, a distance $t_1$) from a plane 240 including a focal point of the radiation source 2 and situated perpendicular to the plane on which the diaphragm plates 214 and 216 are located. The diaphragm plates 214 and 216 have the end surfaces 226 and 228 which are parallel to the above-mentioned plane 240 including the focal point of the radiation source 2. Likewise, the ends 230, 232 of the diaphragm plates 218 and 220 are spaced a distance $t_2$ away from the above-mentioned plane 240 including the focal point of the radiation source 2 and the diaphragm plates 218 and 220 have respective end surfaces 230 and 232 parallel to the above-mentioned plane 240 including the focal point of the radiation source 2. The distances $t_1$ and $t_2$ are determined by the focal size of the radiation source 2 and the distance from the focal point to the paired diaphragm plates. A pinion 236 is located at the other end portion of the diaphragm plate 214 and engages with a rack 234 formed on the surface of the diaphragm plate 214.

The pinion 236 is rotated by a motor 238. A second pinion 236a is provided at the other end portion of the other diaphragm plate 216 and engaged with a rack 234a formed on the diaphragm plate. The pinion 236a is connected to the motor 238a. Likewise, other pinions (not shown) are provided at the other end portion of each of the other diaphragm plates 218 and 220 and engaged with racks formed on each of these diaphragm plates. Each pinion is connected to a control motor. The respective diaphragm plates may be moved by another means which is used in place of the motors shown. The variable diaphragm 6 in FIG. 10 has a means for detecting the amount of movement of each of the diaphragm plates 214, 216, 218 and 220, for example, a laser source 215, light receiving element 217 and light shielding means (not shown). When in such variable diaphragm 6 the control motors are driven, the respective pinions 236, 236a, 236b and 236c are driven to cause the diaphragm plates 214, 216, 218 and 220 to be moved through the respective racks 234, 234a, 234b and 234c formed thereon. The values of the distances $t_1$ and $t_2$ are varied by the movement of these diaphragm plates. When the distances $t_1$ and $t_2$ reach a predetermined value, the motors are stopped and a radiation beam is emitted from the radiation source 2 and passed through the gap $2t_1$ between the diaphragm plates 214 and 216 and the gap $2t_2$ between the diaphragm plates 218 and 220 to obtain a fan-shaped beam 4 of included angle $\alpha$. The included angle of the fan-shaped beam can be varied by moving the diaphragm plates. The reason why the variable diaphragm 6 comprises the paired diaphragm plates 214, 216 and 218, 220 is that the radiation source 2 has a face focal point, not a point focal point. If the variable diaphragm 6 is constructed of the pair of diaphragm plates 218, 220 only, a direct beam 242 and penumbra 244 shown in FIG. 11 from the radiation source 2 are directed toward the subject, making the tomographic image data inaccurate.

Figure 12:
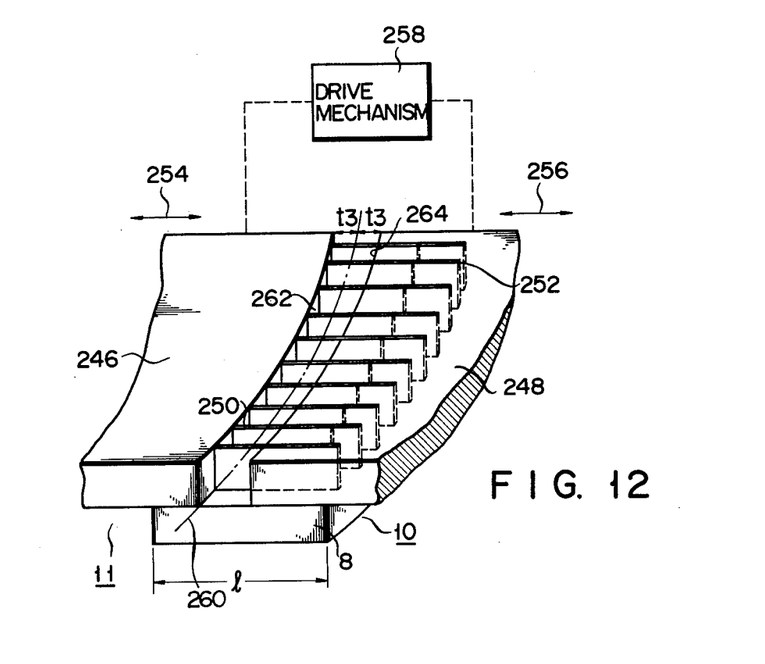
FIG. 12 is a perspective view schematically showing one form of variable collimator as incorporated in the apparatus according to the invention.

The slot length of the variable collimator 11 shown in FIG. 12 can be varied by restricting the radiation beam falling onto the respective radiation detection cells 8 of the radiation detector 10 according to the width of a variable slit 7. The collimator 11 is formed in an arcuate pattern so as to have its top surface equidistantly spaced apart from the radiation source 2 and has shielding plates 246 and 248 having a substantially equal thickness throughout the whole area thereof. A plurality of partition walls 250 are mounted on one of these shielding plates 246 and 248 and have a height equal to the thickness of the shielding plates. The spacing between the partition walls 250 is equal to the width of each radiation detection cell 8 of the radiation detector 10 on which the variable collimator 11 is placed. Grooves 252 equal in number to the partition walls 250 are formed in the other shielding plate 248. One shielding plate 246 has its partition walls inserted into the corresponding grooves of the other shielding plate 248, and these shielding plates are moved by a drive device 258 in a direction indicated by arrows 254, 256 so that the end surfaces 262 and 264 of the shielding plates 246 and 248 are equidistantly spaced apart from a center line 260 of the radiation detector 10. The drive mechanism 258 is driven according to the opening width of the variable slit 7. The drive mechanism 258 may be driven either manually or by a drive means such as a motor etc. The maximum value of the gap $2t_3$ between the shielding plates 246 and 248 may be determined to be smaller than the length 1 of the detection plane on the radiation detection element 8. The gap $2t_3$ between the shielding plates 246 and 248 is varied by the movement of the shielding plates 246 and 248 to permit a variation of the collimating width, i.e., the thickness of the radiation beam separated by each partition wall 250. As a result, even if the width of the slit 7 is varied, for example, each detection element 8 on the radiation detector 10 can detect all the radiation beam passed through the to-be-examined subject 20.

It will be apparent to those skilled in the art that various modifications and variations can be made in the et scanner of the present invention without departing from the scope or spirit of the invention. Thus, it is intended that the present invention cover all such modifications and variations provided they come within the scope of the appended claims and their equivalents.

What is claimed is:

1. A computed tomography scanner comprising a radiation source for irradiating a subject with a diverging pattern of beams of penetrating radiation; a radiation detector disposed opposite to said radiation source with the subject therebetween to detect the radiation penetrating said subject and to generate electrical signals proportional to the radiation intensity detected in said beams; signal processing means for analyzing the pattern of radiation absorption coefficients for the cross-sectional area of said subject irradiated by said beams based on the electrical signals produced by said radiation detector; rotation means for rotating said radiation source and said radiation detector around said subject to scan said cross-sectional area; and means for shifting the rotation loci of said radiation source and said radiation detector relative to said subject to position said cross-sectional area within said diverging beam pattern so as to intersect a maximum number of said beams.

2. The apparatus according to claim 1, further including a variable diaphragm for permitting varying the angle at which said diverging beam pattern is spread.

3. The apparatus according to claim 1, further including a variable dimension slit for permitting varying the beam thickness of said diverging beam pattern.

4. The apparatus according to claim 1, further including a variable dimension collimator for changing the thickness of said diverging beam pattern as received by said radiation detector.

5. Apparatus according to claim 1, in which said means for shifting includes a support frame for supporting said radiation source and said radiation detector and means for moving said frame in a direction perpendicular to the rotation axis of said radiation source and radiation detector.

6. Apparatus according to claim 5, in which said rotation means includes a rotation support for supporting said support frame and rotation drive means for rotating said rotation support.

7. A computed tomography scanner comprising:
radiation source means for projecting a substantially fan-shaped radiation beam to a subject to be examined;
detector means for detecting the radiation penetrating said subject and for generating a detector output representing the intensity of portions of said beam intersecting different points within said subject;
means for supporting said radiation source means and said detector means;
means for converting said detector output into electrical signals to permit display of a reconstructed image of said subject;
means for rotating said supporting means around said subject in order to effect a scan thereof;
means for shifting said radiation source means and said detector means on said supporting means in accordance with the size of said subject while the center of rotation of said supporting means remains unchanged;
first means for controlling the width of said radiation beam;
second means for controlling the thickness of said radiation beam, said second means being disposed together with said first means between said radiation source means and said subject; and
third means for collimating said radiation beam penetrating said subject.

8. The computed tomography scanner according to claim 7, in which said first means is adjustable to provide an included angle of said fan-shaped radiation beam in accordance with the size of said subject.

9. The computed tomography scanner according to claim 7, in which said second means includes variable slit means for adjusting the thickness of said fan-shaped radiation beam in accordance with the size of said subject.

10. The computed tomography scanner according to either of claims 8 or 9, in which said third means includes a variable collimator for adjusting the collimation of said radiation beam penetrating said subject, said adjustment being made in accordance with the magnitude of the included angle and the thickness of said radiation beam emitted by said radiation source means.

11. The computed tomography scanner according to claim 7, in which said support means includes a support frame and said rotation means includes rotation drive means for moving said frame in a direction perpendicular to the rotation axis of said radiation source means and said detector means.

12. A computed tomography scanner comprising:
a radiation source for projecting a substantially fan-shaped radiation beam to a subject to be examined;
a plurality of detectors for detecting portions of said radiation beam penetrating said subject, said detectors being arranged at a fixed distance from said radiation source and generating electrical signal outputs representing the intensity of the radiation detected thereby;
a central processor for processing said electrical signal outputs produced by said detectors to reconstruct an image of said subject;
a display device for displaying the reconstructed image of said subject;
a support member for mounting said radiation source and said detectors;
a rotation support holding said support member, said rotation support including an aperture to receive said subject;
a shifting mechanism for shifting said support member relative to said rotation support to adjust the position of said radiation source and detectors in accordance with the size of said subject;
a rotating mechanism for rotating said rotation support while the center of rotation thereof remains unchanged no matter how said radiation source and said detectors are shifted by said shifting mechanism;
a variable diaphragm for controlling the width of said radiation beam in accordance with the size of said subject;
a variable slit for controlling the thickness of said radiation beam in accordance with the size of said subject, said diaphragm and said slit being disposed between said radiation source and said subject; and
a plurality of collimators for collimating the portion of said radiation beam penetrating said subject.

13. The computed tomography scanner according to claim 12, in which said collimators are adjusted to control the collimation of said radiation beam penetrating said subject in accordance with the width and the thickness of said radiation beam set by said diaphragm and said slit respectively.

14. The computed tomography scanner according to claim 13, in which said variable collimators include partition grooves and a movable shielding plate for controlling the thickness of the portion of said radiation beam detected by said radiation detectors.

15. The computed tomography scanner according to claim 12, in which said diaphragm includes at least two pairs of diaphragm plates spaced apart from one another in a direction transverse to the axis of said beam for controlling the width of said radiation beam.

16. In a computed tomography scanner having a radiation source adapted to emit a diverging pattern of radiation for irradiating an area of a subject under examination and having a plurality of radiation detectors positioned at a fixed distance from said source for detecting radiation penetrating said subject to enable construction of a tomographic image of said area, said source and said detectors being movable past said area to effect a scan thereof, the combination comprising:
means for supporting said subject within said pattern of radiation to expose said area for examination; and
means for adjusting the position of said source and said detectors relative to said support means to shift said area within said diverging pattern of radiation to maximize the amount of radiation which intersects said area under examination, whereby the resolution of said constructed tomographic image is substantially unaffected by the size of said area.

17. The apparatus of claim 16 in which said means for adjusting comprises:
first frame means mounted for rotatable movement about said subject; and
second frame means for shiftably supporting said radiation source and said detectors on said first frame means so that the position of said source and said detectors can be moved relative to said subject without changing their center of rotation.

* * * * *